United States Patent [19]
Holtom et al.

[11] Patent Number: 6,108,081
[45] Date of Patent: Aug. 22, 2000

[54] NONLINEAR VIBRATIONAL MICROSCOPY

[75] Inventors: Gary R. Holtom; Xiaoliang Sunney Xie, both of Richland, Wash.; Andreas Zumbusch, München, Germany

[73] Assignee: Battelle Memorial Institute, Richland, Wash.

[21] Appl. No.: 09/294,834

[22] Filed: Apr. 19, 1999

Related U.S. Application Data

[63] Continuation-in-part of application No. 09/120,035, Jul. 20, 1998, abandoned.

[51] Int. Cl.[7] .............................. G01J 3/44; G01N 21/65
[52] U.S. Cl. ............................................. 356/301
[58] Field of Search ................................. 356/301, 317, 356/318

[56] References Cited

U.S. PATENT DOCUMENTS

| | | | |
|---|---|---|---|
| 4,077,719 | 3/1978 | Barrett et al. | 356/301 |
| 4,405,237 | 9/1983 | Manuccia et al. | 356/301 |
| 4,512,660 | 4/1985 | Goldberg | 356/301 |

OTHER PUBLICATIONS

Duncan et al, Optics Letters, vol. 7, No. 8, Aug. 1982, pp. 350–352.

*Primary Examiner*—F. L. Evans
*Attorney, Agent, or Firm*—Paul W. Zimmerman

[57] ABSTRACT

The present invention is a method and apparatus for microscopic vibrational imaging using coherent Anti-Stokes Raman Scattering or Sum Frequency Generation. Microscopic imaging with a vibrational spectroscopic contrast is achieved by generating signals in a nonlinear optical process and spatially resolved detection of the signals. The spatial resolution is attained by minimizing the spot size of the optical interrogation beams on the sample. Minimizing the spot size relies upon a. directing at least two substantially co-axial laser beams (interrogation beams) through a microscope objective providing a focal spot on the sample; b. collecting a signal beam together with a residual beam from the at least two co-axial laser beams after passing through the sample; c. removing the residual beam; and d. detecting the signal beam thereby creating said pixel. The method has significantly higher spatial resolution then IR microscopy and higher sensitivity than spontaneous Raman microscopy with much lower average excitation powers. CARS and SFG microscopy does not rely on the presence of fluorophores, but retains the resolution and three-dimensional sectioning capability of confocal and two-photon fluorescence microscopy. Complementary to these techniques, CARS and SFG microscopy provides a contrast mechanism based on vibrational spectroscopy. This vibrational contrast mechanism, combined with an unprecedented high sensitivity at a tolerable laser power level, provides a new approach for microscopic investigations of chemical and biological samples.

40 Claims, 8 Drawing Sheets sample height

NONLINEAR VIBRATIONAL MICROSCOPY

CROSS REFERENCE TO RELATED INVENTION

This application is a Continuation-In-Part of application serial No. 09/120,035 filed Jul. 20, 1998, now abandoned.

This invention was made with Government support under Contract DE-AC0676RLO1830 awarded by the U.S. Department of Energy. The Government has certain rights in the invention.

FIELD OF THE INVENTION

The invention relates to obtaining an image pixel by nonlinear vibrational spectroscopy.

BACKGROUND OF THE INVENTION

Two-photon fluorescence microscopy (Denk, Strickler, Webb, U.S. Pat. No. 5,034,613) and confocal-fluorescence microscopy (See "Confocal Microscopy" SPIE Milestone Series, 1996, ISBN 0-8194-2372-6, edited by Barry Master for original papers and patents) for three-dimensional optical imaging have made a significant impact in many disciplines, especially cell biology. Fluorescence microscopy requires either intrinsic fluorescence or staining with a fluorescent dye. Both of these methods lack generality, and adding dyes affects the properties of biological specimens. In confocal microscopy a pinhole in the optical path restricts detection to a small focal volume element, thereby efficiently reducing signal background and improving image contrast. In two-photon microscopy the excitation volume is restricted by virtue of a nonlinear process in which two photons from a pulsed laser source are simultaneously absorbed. Both of these techniques allow the reconstruction of three-dimensional images.

For chemical species or cellular components that either do not fluoresce or cannot tolerate labeling, Infrared (IR) microscopy or spontaneous Raman microscopy can be used. In these cases, vibrational spectroscopy provides the contrast mechanism. Direct imaging using IR light absorption in a microscope has been used. However, the spatial resolution of this technique is low (~10 $\mu$m) due to the long wavelength of the light used. Three-dimensional spontaneous Raman microscopy of biological samples has been demonstrated with a confocal microscope as reported by Puppels, G. J., de Mul, F. F. M., Otto, C., Greve, J., Robert-Nicoud, M., Arndt-Jovin, D. J. & Jovin, T. M. Studying single living cells and chromosomes by confocal Raman microspectroscopy. *Nature* 347, 301–303 (1990); Sijtsema, N. M, Wouters, S. D., De Grauw, C. J., Otto, C. & Greve, J. Confocal direct imaging Raman microscope: Design and applications in biology. *Appl. Spectrosc.*, 52, 348–355 (1998). The intrinsically weak Raman signal necessitates high laser powers (typically>10 mW) and is often overwhelmed by the fluorescence background of the sample.

Two nonlinear techniques have been demonstrated for vibrational spectroscopy. The first technique is Coherent Anti-Stokes Raman Scattering (CARS), described e.g. in Shen, Y. R. *The Principles of Nonlinear Optics* (John Wiley & Sons Inc. New York, 1984),267–275, is a nonlinear optical four-wave-mixing process containing vibrational spectroscopic information. A schematic diagram of this process is given in FIG. 1A (prior art). For CARS spectroscopy, a pump laser and a Stokes laser beam, with center frequencies of $\omega p$ and $\omega s$, respectively, are spatially overlapped. When the frequency difference $v_p - v_s$ coincides with the frequency of a vibrational transition of the sample, a strong CARS signal at $v_{as} = 2v_p - v_s$ is generated in a direction determined by the phase-matching conditions (FIG. 1A.) The intensity of the detected signal, $I_{AS}$, is proportional to the square modulus of a molecular term $\chi^{(3)}$ times the pump intensity $I_P$ squared, times the Stokes wave intensity $I_S$.

$$I_{AS} = I_P^2 \cdot I_S \cdot |\chi^{(3)}|^2$$

$\chi^{(3)}$ includes terms for a resonance enhancement at certain molecular vibration frequencies. Because the process is cubic in laser power, the signal is only generated efficiently with high excitation intensities. It is therefore advantageous to use high peak power which are readily available from femtosecond or picosecond light pulses.

U.S. Pat. No. 4,405,237 to Manuccia and Reintjes discusses a Coherent Anti-Stokes Raman spectroscopy device for microscopic imaging or observing cellular constituents in live samples. In their proposed scheme, two parallel, but not overlapping laser beams are focused to a common focal spot. The two laser beams are provided by two lasers tunable to wavelengths of 565–620 nm and 620–700 nm respectively as reported in Scanning coherent anti-Stokes Raman microscope, M D Duncan, J Reintjes, T J Manuccia, Optics Letters, Vol. 7, No. 8, Aug. 1982. They collect and detect the signal beam in the phase matched condition. In this case, however, the cone angles of the two beams are small, which means that the size of the focal spot is large (10 micron Duncan et al., 1982), and the spatial resolution is low. This was not a confocal arrangement therefore high resolution three-dimensional sectioning capability was not achievable. Moreover, the sensitivity of CARS microscopy was limited by the nonresonant background signal. The magnitude of the non-resonant background signal is dependent on the wavelengths of the excitation lasers. With visible wavelength lasers, the CARS signal is dominated by the non-resonant background signal. These intrinsic difficulties have limited the experimental demonstration and application of this proposed scheme.

An article by Zhao et al., The wave-mixing near field optics amplifiers: a theoretical feasibility study for nonlinear NFO experiments in biology chemistry and materials science, Elsevier, Ultramicroscopy 61 (1995) 69–80, discusses a method of using near field optics to conduct nonlinear spectroscopy, including Coherent Anti-Stokes Raman spectroscopy. Zhao et al. proposed wave mixing with a first laser light at a first frequency and a second laser light at a second frequency that both impinge on a sample slab. The feasibility was discussed for a situation in which the first laser light emerges from an aperture probe and the second laser light be incident at a non-normal angle. This configuration for near-field CARS, intending for a high spatial resolution beyond the diffraction limit, requires a feedback system regulating the probe-sample distance and has not yet been experimentally demonstrated.

The second nonlinear vibrational spectroscopic technique is Sum Frequency Generation (SFG), as described e.g. in Shen, Y. R. *The Principles of Nonlinear Optics* (John Wiley & Sons Inc. New York, 1984), 67—85. Sum Frequency Generation is a nonlinear process requiring two incident laser beams with frequency of $v_s$ and $v_p$ focused to a common spot, generating a new frequency $v_{sf} = v_s + v_p$ and providing vibrational contrast when $v_s$ is on resonance with molecular vibration. The energy diagram and phase matching diagram are shown in FIG. 1B. Distinctions of SFG from CARS include (1) The SFG process is a $\chi^{(2)}$ effect and depends linearly on the intensity of each incident beam, (2)

The sensitivity of SFG to vibration requires one of the lasers be infrared (IR), so that its frequency ($v_1$) is in resonance with that of a vibrational transition of the sample (3) the IR beam is absorbed by the sample (4) the signal beam is produced only at a surface, which is very useful for surface specific information generally unavailable by other means. Microscopy with SFG has not been demonstrated.

Imaging with third harmonic generation, another coherent four-wave-mixing process, has been demonstrated by Barad, Y., Eisenberg, H., Horowitz, M. & Silberberg, Y. Nonlinear scanning laser microscopy by third harmonic generation *Appl. Phys. Lett.* 70, 922–924 (1997); Muller, M., Squier, J., Wilson, K. R. & Brakenhoff G. J. 3D-microscopy of transparent objects using third-harmonic generation. *J. Microsc.*, 191, 266 (1998) This technique is similar to CARS microscopy in that the signal is dependent on the third-order polarizability $\chi^{(3)}$, but differs in that it probes the electronic contributions to $\chi^{(3)}$ not specifically sensitive to vibrational properties. The electronic contributions to $\chi^{(3)}$ are exhibited as a weak non-resonant background signal in CARS microscopy.

Hence, there is a need in the art for a method and apparatus for nonlinear vibrational microscopy that is sensitive to vibrational properties, has high sensitivity and high spatial resolution, and has a straightforward implementation.

SUMMARY OF THE INVENTION

The present invention is a method and apparatus for nonlinear microscopic vibrational imaging. Microscopic imaging incorporating vibrational spectroscopic information is achieved by spatial resolution of detected signals a pixel at a time. The spatial resolution is attained by minimizing the spot size of the optical interrogation beams on the sample. Nonlinear vibrational microscopy relies on a. directing at least two substantially co-axial laser beams (interrogation beams) having first and second frequencies (different colors or wavelengths) through a microscope objective providing a common focal spot on the sample;

b. collecting a signal beam (e.g. CARS or SFG) together with at least two residual beams from the at least two co-axial laser beams after passing through the sample;

c. removing the at least two residual beams; and d. detecting the signal beam thereby creating said pixel. Because each laser beam produces a residual beam, it is preferred to remove all residual beams. Removing is defined as spectrally separating the residual beam(s) from the signal beam.

Another embodiment of the present invention is an improvement to the steps of creating a pixel, or spatially resolved image element, from at least two laser beams having first and second frequencies, the at least two laser beams spatially coincident on a sample producing a signal beam of a new frequency, the method having the steps of:

a. directing the at least two laser beams through a lens providing a common focal spot on the sample;

b. collecting the signal beam together with at least two residual beams from the at least two laser beams after passing through the sample;

c. removing the at least two residual beams; and d. detecting the signal beam thereby creating said pixel; wherein the improvement is:

at least one of the at least two laser beams has a wavelength in the range of from deep red ( greater than 0.7 micron) to near infrared (2 micron).

A preferred apparatus has (a) a pump wave laser that is a Ti:S mode-locked laser amplified with a regenerative amplifier operating at 250 kHz for generating a pump beam; (b) a second beam provided by an optical parametric oscillator amplified with an optical parametric amplifier, pumped by the regenerative amplifier; (c) telescopes for collimating and expanding the beams, plus a dichroic mirror for making the beams coaxial; (d) a microscope objective lens for focusing said pump wave laser and said second wave laser onto a sample; and (e) a blocking filter that passes a signal beam to a detector, and (f) a detector to detect the signal beam.

According to the present invention, the incident laser beams are expanded to fill the back aperture of the objective lens. The objective lens has a high numerical aperture to obtain a small focal spot on or within the sample. Creating a small excitation volume results in efficient background signal rejection and reduced photodamage to the sample, and allows three-dimensional microscopy by sectioning at different focal planes. The nonlinear intensity dependence restricts the excitation to a small volume at the laser foci, similar to two-photon fluorescence microscopy. The effective excitation volume at the focus is somewhat smaller than the diffraction limit as usually defined.

An image can be generated either by raster scanning the focal spot over the sample using a galvanometer scanner or by raster scanning the sample through the fixed focal spot with a xy translation stage. In this manner a series of pixels is generated to form a two-dimensional image. By moving the sample along the z-axis with respect to the focal spot, images of planes at different depths can be produced, allowing a three-dimensional image to be constructed.

For CARS microscopy, visible to near infrared (0.4–1.5 μm wavelength) may be used. However, deep red to near-infrared (greater than 0.7–1.5 μm wavelength) excitation beams are preferred because they do not usually give rise to electronic excitations in the sample and therefore avoid photochemical damage due to photobleaching. The long excitation wavelengths also minimize Rayleigh scattering in heterogeneous samples and consequently provide large penetration depths for thick samples that are desirable for many applications including but not limited to biomedical applications.

The present invention of CARS microscopy is similar to confocal and two-photon fluorescence microscopy in that the signal is generated only at the focal spot of the microscope objective, allowing three-dimensional imaging. CARS microscopy differs from confocal and two-photon fluorescence microscopy in that CARS provides a vibrational contrast and requires no fluoropores.

A major difference between CARS microscopy and spontaneous Raman microscopy is that CARS is a coherent process, in which the molecular vibrations in the excitation volume oscillate in phase, interfering constructively. Therefore, the CARS signal is proportional to the square of the concentration of the vibrational modes. In contrast, a spontaneous Raman or fluorescence signal is incoherent and has linear concentration dependence. A major advantage of CARS microscopy over spontaneous Raman microscopy is that CARS microscopy is much more sensitive and requires less average excitation power.

The present invention of CARS microscopy differs from the previous schemes for CARS imaging in that the two incoming beams are tightly focused to create a smaller spot, which results in higher sensitivity and higher spatial resolution. The phase-matching conditions are relaxed because of the large cone of wave vectors and the short interaction length, generating a large cone of signal beam which is separated from pump and Stoke beam spectrally (rather than spatially).

The present invention is useful for various applications. CARS and SFG microscopy can find use in a variety of different fields such as biological sciences, material science, medical diagnosis, or food processing, to name a few. For example, biological applications open up many new possibilities. Most biological samples have a substantial water content and will be in an aqueous medium. This is fortunate for two reasons: water has a weak Raman signal, and it is an excellent medium for removing heat deposited by the laser beams, if any. Furthermore, based on experiments with viable cell cultures using femtosecond Ti:S lasers, it is expected that the imaging process do not harm living cells at the averaged power level used. Being surface sensitive, SFG microscopy will find wide applications to biological membranes. Similarly, polymer or ceramic materials can be interrogated by CARS and SFG microscopy. The organic or inorganic sample can be analyzed by CARS SFG spectroscopy for chemical identities, and imaged to characterize polyphasic or multiple components.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1B:
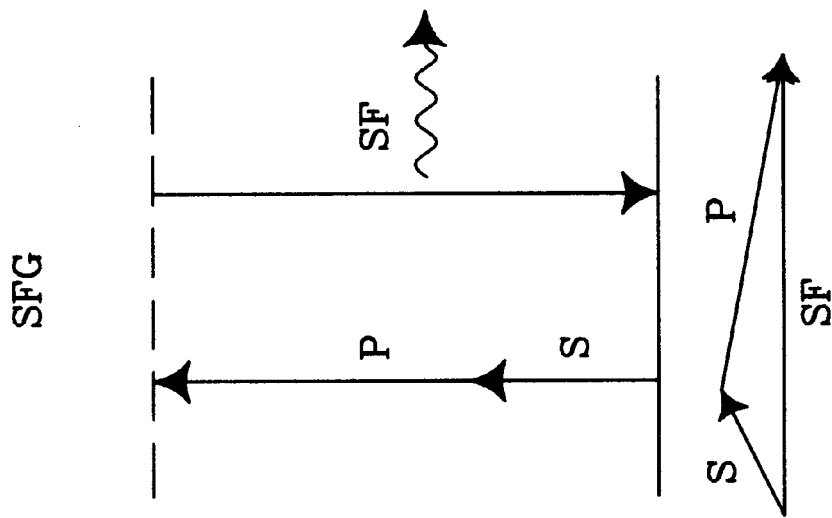
FIG. 1b is an energy level and phase matching diagram of laser beams used in SFG (prior art).
Figure 1A:
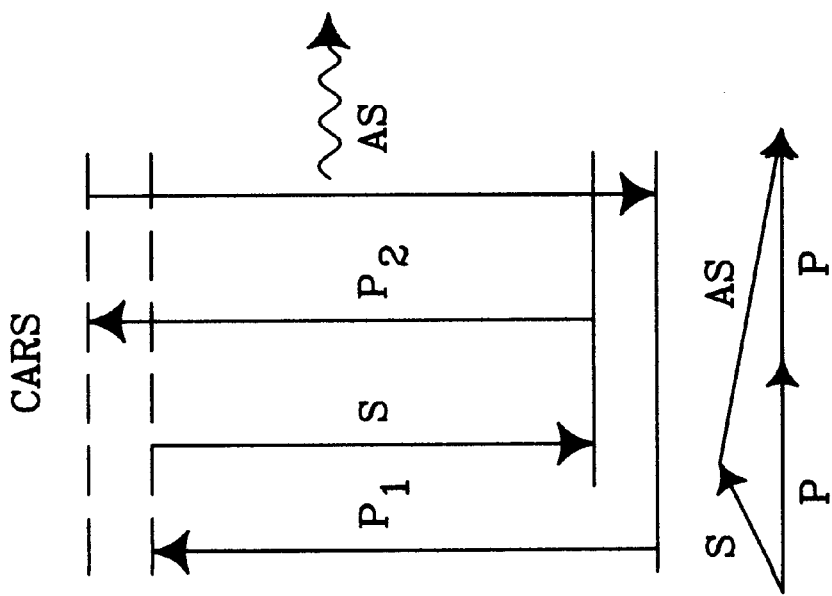
FIG. 1a is an energy level and phase matching diagram of laser beams used in CARS (prior art).

The present invention is a method and apparatus for nonlinear microscopic vibrational imaging. Microscopic imaging incorporating vibrational spectroscopic information is accomplished by spatial resolution of detected signals optimized by minimizing the spot size of the optical interrogation beams on the sample. Each spot creates an image pixel that is correlated to a position, so that collecting multiple spots or pixels may provide a 2-D or three-dimensional image. Obtaining an image pixel relies upon a. directing at least two substantially co-axial laser beams (interrogation beams) having first and second frequencies (different colors or wavelengths) through a microscope objective providing a common focal spot on the sample;

b. collecting a signal beam together with a residual beam from the at least two co-axial laser beams after passing through the sample;

c. removing the residual beams; and d. detecting the signal beam thereby creating said pixel.

Substantially co-axial is defined as the longitudinal axes of the two beams being within a beam radius apart. With the axes within a beam radius, the two beams overlap. Preferred is 100% overlap with the longitudinal axes co-axial. Substantially co-axial includes substantially parallel wherein there is at least some overlap along the full length of travel of the beams as viewed from one end or the other of the beginning or end of travel of a beam. The beams may approach the objective lens from the same side of the objective lens or opposite sides.

Because each laser beam produces a residual beam, it is preferred to remove all residual beams. Removing is defined as spectrally separating the residual beam(s) from the signal beam.

The beams may be expanded and collimated in order to fill more area of the back aperture of the objective lens than a non-expanded beam set. The objective lens may be of a high numerical aperture, for example an oil immersion, 1.4 NA to focus the beams to about 0.4 micron diameter. Oil and water immersion lenses are used, depending on the medium surrounding the sample. With the tight foci, the phase-matching conditions are relaxed because of the large cone of wave vectors and the short interaction length. The nonlinear intensity dependence restricts the excitation to a small volume at the laser foci. This leads to efficient background signal rejection, reduces photodamage to the sample, and allows three-dimensional microscopy by sectioning at different focal planes. A slight improvement in lateral resolution compared to conventional microscopy is also observed.

It will be appreciated by those of skill in the art that expansion of the laser beams may not be needed by selecting a laser beam size in combination with an objective lens wherein the laser beam size substantially matches the back aperture of the objective lens. It will be further appreciated by those of skill in the art that the lens may be a simple lens. Various combinations of beam size lens type and numerical aperture will provide various resolutions. The desired resolution is, of course, dependent upon the size of the features to be observed or imaged.

An image can be generated either by raster scanning the focal spot over the sample, steering the laser beams using a galvanometer scanner, or by raster scanning the sample through the fixed focal spot with a xy translation stage. In this manner a series of pixels is generated to form a two-dimensional image.

Alternatively or in addition, changing the observed Raman shift given by the frequency difference of two laser beams ($v_P$–$v_S$) may be done for obtaining a vibrational property of the sample.

It is preferred that the Raman shift is less than 4000 cm$^{-1}$ (4000 wavenumbers) the accessible range only being determined by the laser system used.

The method preferably includes the further step of selecting a pulse width for the at least two laser beams, the pulse width being infinite (continuous wave excitation), preferably shorter than infinite, but longer than 1 nanosecond, more preferably between 1 nanosecond and 1 picosecond, most preferably shorter than that. An optical delay line (not shown) is used to temporally overlap the pulse trains of the at least two laser beams. Shorter pulses offer greater signal intensity for the same amount of average power at the sample thereby providing an increased detected signal from the sample for the same amount of energy expended into the sample.

Another embodiment of the present invention improves in the method of creating a pixel, or spatially resolved image element, from at least two laser beams having first and second frequencies, the at least two laser beams spatially coincident on a sample producing a signal beam of a new frequency, the method having the steps of:

a. directing the at least two laser beams through a lens providing a common focal spot on the sample;

b. collecting the signal beam together with at least two residual beams from the at least two laser beams after passing through the sample;

c. removing the at least two residual beams; and d. detecting the signal beam thereby creating said pixel; wherein the improvement is:

at least one of said at least two laser beams has a wavelength in the range of from deep red (greater than 0.7 micron) to near infrared (2 micron).

Further improvement is realized when the at least two laser beams have wavelengths in the range of from deep red to near infrared. In a preferred embodiment, the use of deep red to near infrared wavelength is combined with the first embodiment wherein the at least two laser beams are coaxial, preferably filling a back aperture of the lens thereby providing the common focal spot of a size of less than 10 micron.

The apparatus of the present invention creates a pixel from at least two laser beams having first and second frequencies, the at least two laser beams spatially coincident on a sample producing a signal beam of a third frequency. The system has:

a. an optical beam combiner and director for directing at least two laser beams in a substantially co-axial relationship through b. a microscope objective providing a focal spot on the sample;

c. a collection lens for collecting the signal beam together with at least two residual beams from the at least two laser beams after passing through the sample;

d. a blocking filter for removing the at least two residual beams; and e. a detector for detecting the signal beam thereby creating said pixel.

The at least two parallel pulsed laser beams are preferably substantially co-axial to obtain the smallest possible common focal spot on the sample.

The system further has geometrically scanning of the sample with respect to said focal spot and obtaining a plurality of pixels of known geometric spatial relationship with respect to datum and generating an image therefrom.

The system preferably also includes a separator control for changing the Raman vibrational frequency separation of at least two of the at least two pulsed laser beams for obtaining spectral information of a vibrational property of the sample.

The producing of the signal beam may be accomplished in one of two ways (1) an indirectly resonant method and (2) directly resonant method. The indirectly resonant method (CARS) has at least two lasers, wherein the frequency difference between two laser beams corresponds to a molecular vibration of the sample, preferably molecular vibrational resonance. The directly resonant method (SFG) also has at least two laser beams wherein the frequency of one of the beams corresponds to a molecular vibration of the sample.

Indirectly Resonant Method and Apparatus

Figure 2:
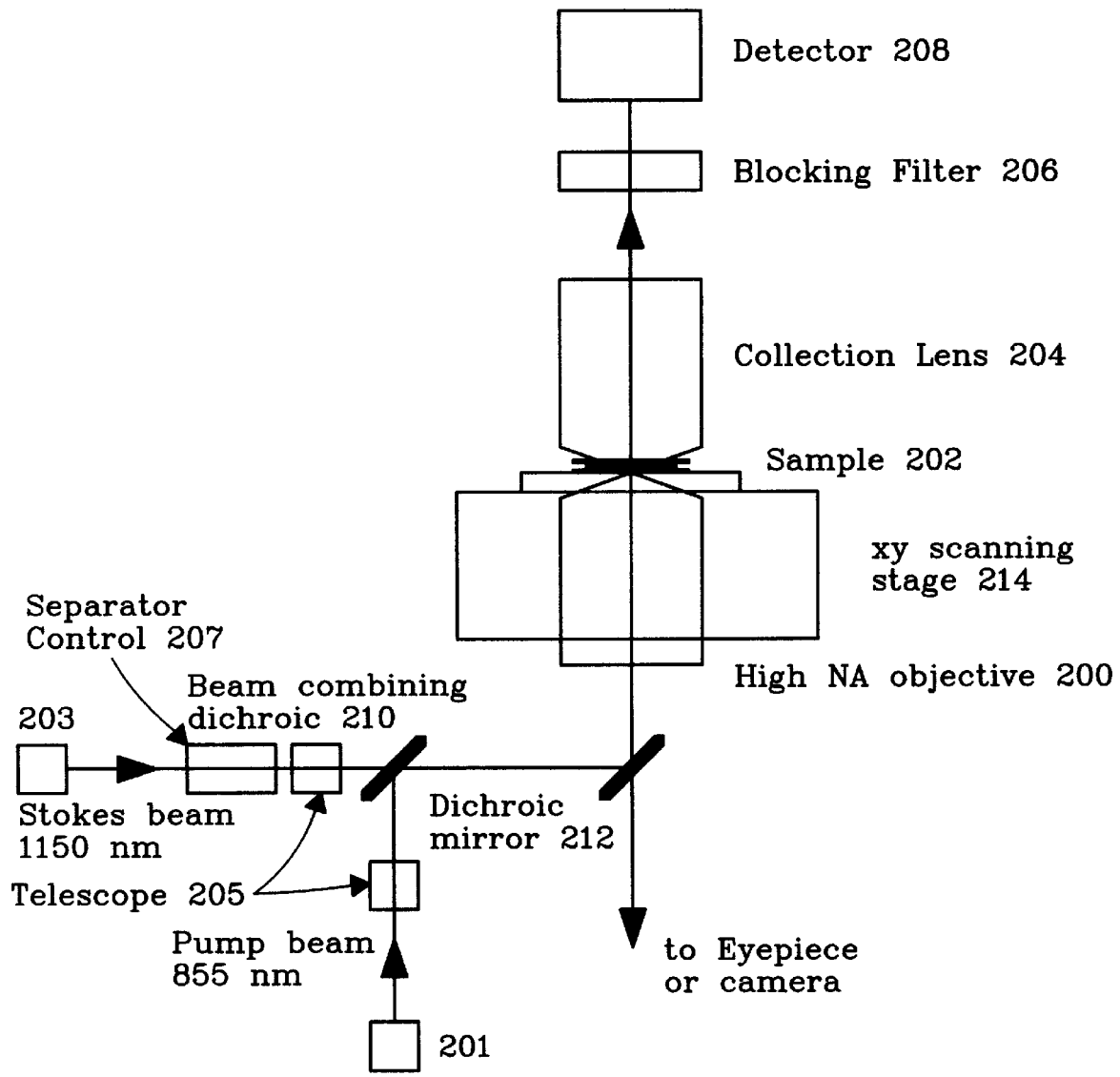
FIG. 2 is a schematic diagram of the apparatus of the present invention.

In order to obtain microscopic imaging with CARS two laser beams are separated by a Raman vibrational frequency of 2600 to 3500 cm$^{-1}$, which covers the fundamental IR absorption region of —OH, —CH, and —NH containing molecules. It is also useful for the laser beams to be in the deep red to near-IR to allow transmission through the sample and to avoid strong absorption and resonance effects with electronic states of the sample. Secondarily, it has been found beneficial to have sub-picosecond (ps) pulse width in order to have substantial peak power. An apparatus (FIG. 2) for CARS microscopic imaging has (a) a pump wave laser 201 that is a Ti:S mode-locked laser amplified with a regenerative amplifier for generating a pump wave $P_1$; (b) a second wave laser 203 that is an optical parametric oscillator having a crystal of KNbO3 amplified with a portion of the pump wave for generating a Stokes wave S; (c) a telescope/mirror (205) for beam collimation and combination; and (d) a microscope objective lens 200 for focusing said pump wave laser and said second wave laser onto a sample 202; and (e) collection lens 204 followed by a blocking filter 206 that passes a detection signal to a detector 208. The Stokes beam S and the pump beam $P_1$ may be combined in a beam combining dichroic optic 210 thereby propagating them substantially co-axially. A beam splitting dichroic 212 may be used to direct the substantially co-axial beams to the sample 202 and to receive an imaging beam. The sample is scanned via a moveable stage 214 to obtain a series of locations of pixels. With the Ti:S mode-locked laser as the pump wave laser, then the second wave laser must operate at a wavelength longer than 1000 nm, which is conveniently generated by an optical parametric oscillator/amplifier (OPO/OPA) system 207 employing KNbO$_3$ crystals, is stable and tunable.

In addition, both the Ti:S laser and the OPO beam are amplified using a regenerative amplifier to provide orders of magnitude more pulse energy at a reduced repetition rate of 250 KHz. Both the higher peak power and lower repetition rate are required to generate strong signals without sample damage from high average powers. A consequence of the short pulses of light is a substantial frequency bandwidth. The Fourier transform limit for the bandwidth of a 100 fs pulse is about 150 cm$^{-1}$, which is comparable to or wider than most vibrational bands. This spectral width can be reduced by using a longer pulse width or by employing a filter. Reducing the spectral bandwidth (at the sacrifice of pulse energy and peak power) produces higher spectral resolution images.

Alternatively a higher repetition rate system can provide sufficient pulse energy but a scheme to reduce the repetition rate may be required in order to obtain high peak power at a certain average power for certain samples. An acousto-optic shutter can produce pulses at an arbitrary repetition rate with low losses. In addition, using picosecond (ps) pulses rather than the fs pulses, has advantages in spectral resolution but drawbacks in signal intensity. CARS microscopy in the femtosecond regime at 250 kHz requires only a moderate excitation average power (~0.1 mW). More than 1 mW may be required for pulses longer than in the femtosecond regime or continues wave lasers at a similar detection level.

Using short and therefore large bandwidth pulses can be exploited to yield detailed spectral information, when the spectral properties of the signal beam are analyzed, e.g. with a monochromator.

EXAMPLE 1

An experiment was conducted to demonstrate the present invention. The apparatus as described above and illustrated in FIG. 2 was used. Specifically, an on-axis optical arrangement was necessary. A blocking filter, consisting of interference filters and/or filter glass, was used to reject the Pump and Stokes beams while transmitting the Anti-Stokes beam. The objective lens was stationary and the sample was supported by the movable inner part of the xy(z) stage to permit imaging by raster scanning the sample.

The test sample was a partial monolayer of polystyrene beads on a glass cover slip. These are available in a variety of tightly controlled sizes, and the size used for this demonstration was 910 nm. These beads had a carboxylated surface, which was optically inactive but improved adhesion to a cover slip. These beads had a strong Raman signal in the 2900 cm$^{-1}$ shift region, but were free of any dyes that would have an electronic one- or two-photon resonance with the laser beams. Since the surface of the beads was corrugated and the microscope objectives were designed to function with a cover glass, usually 170 microns thick, the sample fabrication included coating with an index matching fluid and laying a second cover slip on top of the beads. This sandwich was stable and easily handled. In order to avoid signals from the —CH group in the usual index matching oils, a fluorinated oil was used to surround the beads. This oil was transparent and free of Raman resonances in this region.

The Ti:sapphire (Ti:S) laser at 855 nm (the Pump beam), and a parametrically generated beam at a longer wavelength (the Stokes beam), were incident upon the sample. Two synchronized femtosecond pulse trains at a high repetition rate (250 kHz) were generated from a Ti:sapphire regenerative amplifier (Coherent Rega) operating at a center wavelength of 855 nm and a home-built optical parametric oscillator and optical parametric amplifier operating at 1.1 µm–1.2 µm. The laser system restricts us to the frequency range of 2600 cm$^{-1}$—3300 cm$^{-1}$ for the Raman-shifts, a region typical for C—H and N—H vibrations. However, extension to other spectral regions, such as the fingerprint region at 1000 cm$^{-1}$–2000 cm$^{-1}$, does not pose any notable problems. The two pulse trains are independently adjusted for bandwidths (50 cm$^{-1}$ for each of the beams), temporally overlapped by an optical delay line, co-linearly coupled into an optical microscope, and focused on the same spot of the sample with an oil-immersion objective (Nikon Plan Apo, 60 x, NA 1.4). The sample is raster-scanned with a computerized xy-stage (Physik Instrumente E-500), z-positioning being done with an independent piezo-electric element. The CARS signal is collected in the forward direction with another identical objective lens, filtered for the emission at 665–700 nm and detected with photon counting.

The frequency difference between the beams corresponded to a molecular resonance of about 2900 cm$^{-1}$, according to the molecular group to be brought into resonance. In this process, two pump photons were used to create an additional photon in the Stokes beam along with a new Anti-Stokes photon at about 670 nm. Very short light pulses about 100 femtosecond (fs) long at a repetition rate of 250 kHz were generated permitting rapid data collection with strong signals, with low, non-damaging average power incident on the sample. In addition, the frequency of the Stokes wave (about 1150 nm) was tunable to permit selection of different vibrational frequencies, providing an imaging method with vibrational spectral resolution.

Figure 3:
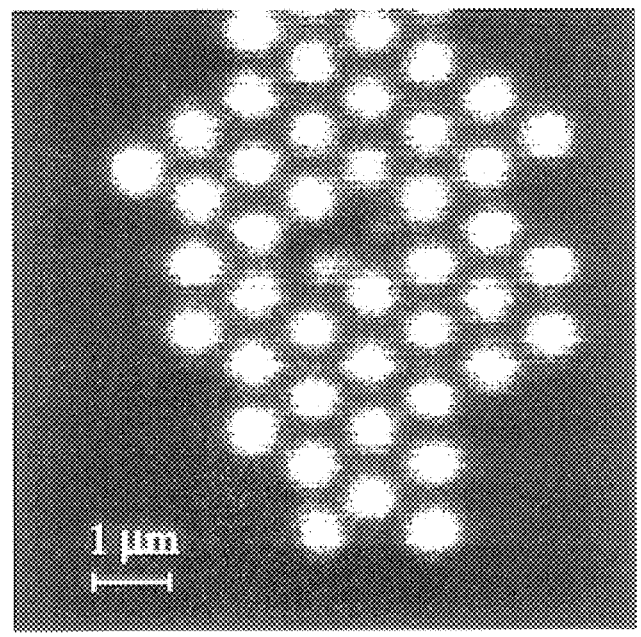
FIG. 3 is a CARS microscopic image of 910 nm diameter polystyrene beads.

With the beams strongly focused, achieved with an oil immersion microscope objective having a numerical aperture (NA) of 1.4, the entire signal was generated from an ellipsoidal focal region with a diameter of less than 0.5 micron and a height of about 1.5 microns. A raster scan of 512 by 512 pixels, covering a dimension of 10 by 10 microns, was taken in about 10 minutes and produced the microscopic image shown in FIG. 3.

Figure 4:
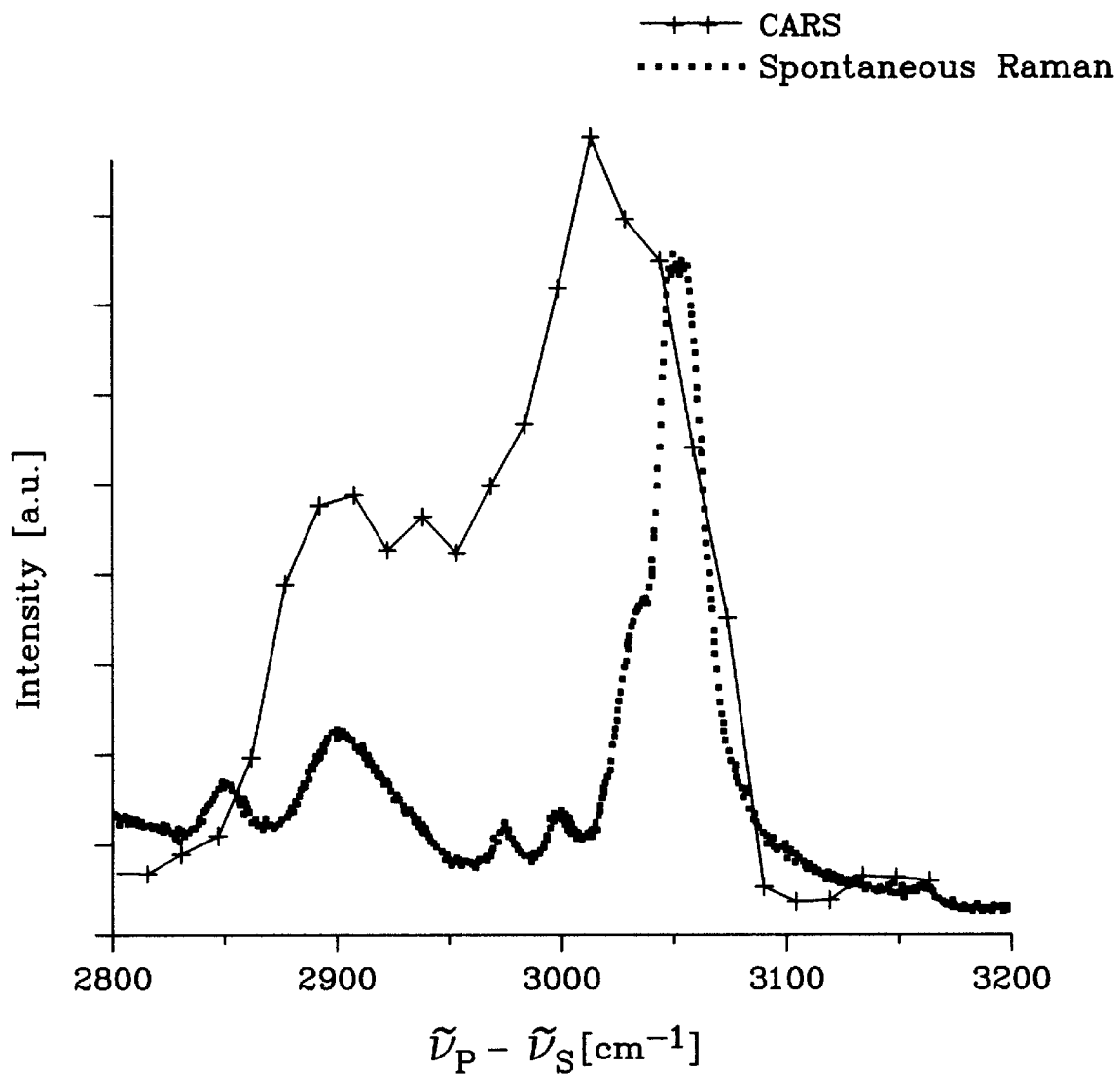
FIG. 4 is CARS spectrum (crosses with solid line) compared to a spontaneous Raman spectrum (dotted line) of a 910 nm diameter polystyrene bead having aliphatic CH ($2851$ $cm^{-1}$ and $2902$ $cm^{-1}$) and aromatic CH ($3054$ $cm^{-1}$) vibrations.

FIG. 4 solid line shows the CARS spectrum of a single carboxylated polystyrene bead of 910 nm diameter on a glass cover slip, centered to the foci. To record the spectrum, the pump wavelength was held constant at $\lambda_p$=854 nm, while the Stokes wavelength was tuned in 2 nm steps from $\lambda_s$=1.12 µm to 1.17 µm, corresponding to Raman-shifts from 2781 cm$^{-1}$–3163 cm$^{-1}$. A weak non-resonant CARS background was present that scaled with intensity in the same way as the resonant CARS signal. The resonant CARS signal was normalized with this background signal in order to compensate for intensity variations associated with the wavelength changes of the Stokes beam. The spectral resolution, given by the convolution of the spectral widths of the two exciting laser beams, lay around 50 cm$^{-1}$. Using longer laser pulses with a narrower spectrum would allow distinguishing sharper spectral features. For comparison, the spontaneous Raman spectrum of the same beads is also shown in FIG. 4 as a broken or dashed line. The peaks at 2851 cm$^{-1}$ and 2902 cm$^1$ are assigned to aliphatic C—H stretching vibrations, while the band at 3054 cm$^{-1}$ is due to an aromatic C—H stretching vibration. The peaks for the aliphatic and aromatic C—H vibrations are also reproduced by the CARS spectrum, which proves the ability of CARS microscopy to differentiate between these spectral features in polystyrene. The dip in the CARS spectrum at 3110 cm$^{-1}$ is reproducible and is caused by destructive interference of the resonant CARS signal with the non-resonant background.

Figure 5:
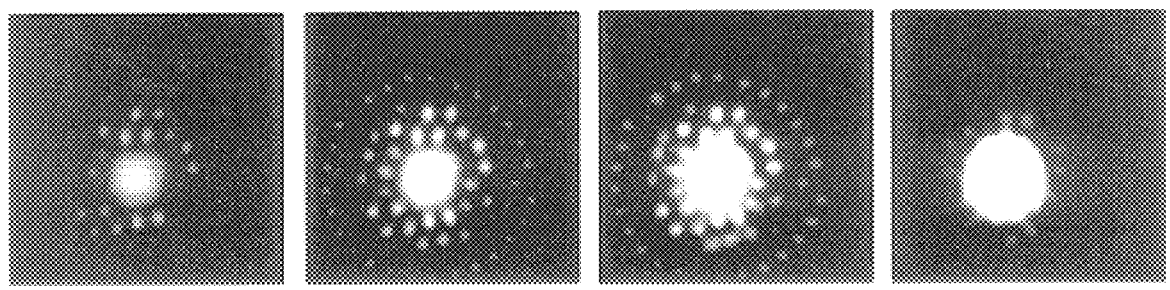
FIG. 5 is a series of 2-D images at sample height increments of 1.2 $\mu$m wherein the movement of the smaller beads into and out of the focal plane is clearly visible. From these data a point spread of function with a FWHM of 1.61 $\mu$m in the axial direction reduced.

A three-dimensional CARS images is shown in FIG. 5, displaying images of a 4.3 µm diameter polystyrene bead surrounded by 910 nm diameter polystyrene beads, recorded at five successive heights from the surface of the glass cover slip with 1.2 µm increments. The movement of the smaller beads in and out of the image plane and the increasing diameter of the large bead in the image plane is clearly seen.

Figure 6:
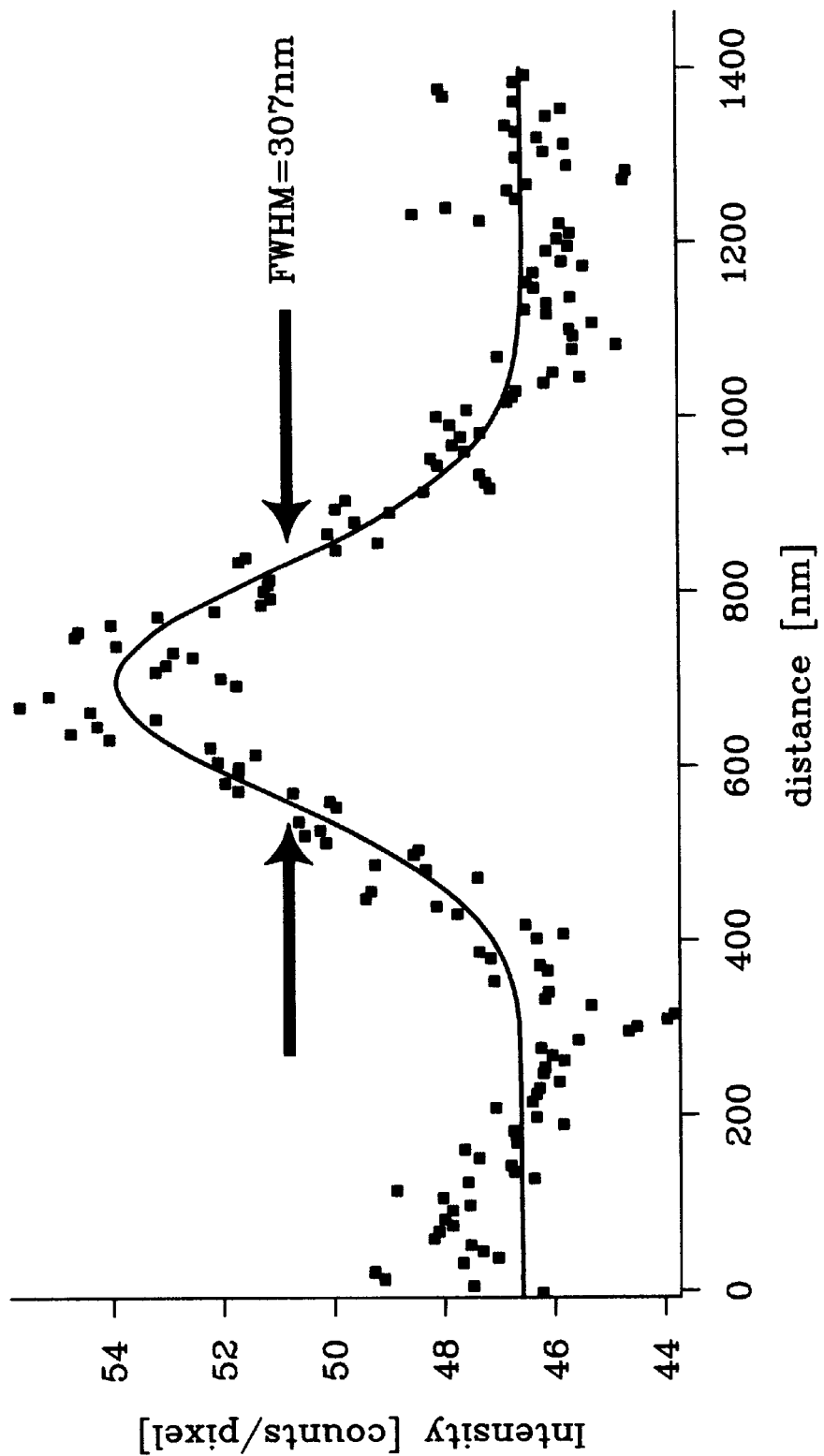
FIG. 6 is a intensity profile from a CARS image of 110 nm diameter polystyrene beads with a fitted Gaussian function (solid line). Collection time for each pixel was 13 ms

In a determination of the sensitivity and lateral resolution, the size of the beads was decreased. Polystyrene beads of 110 nm diameter were easily be imaged. As shown in FIG. 6, the known cross-section for 110 nm beads also allows determining the lateral point spread function with FWHM of 302 nm, which is better than $\lambda/2$ for the excitation wavelengths. One of these beads contained $3.2 \times 10^6$ aromatic rings, which gives an upper limit for CARS detection sensitivity under the moderate power levels used and experimental conditions to be perfected. The limiting factor in imaging small samples is the nonresonant signal generated by the substrate and surrounding medium.

EXAMPLE 2

Figure 7:
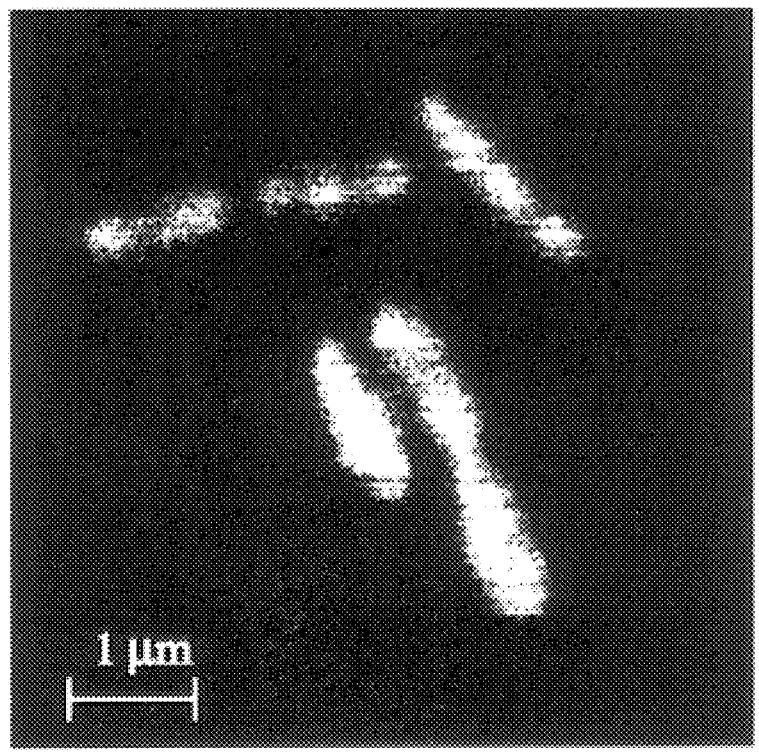
FIG. 7 is a CARS image of three live, unstained HeLa cells in aqueous HEPES buffer solution. Average powers incident at the sample were 50 $\mu$W at 853 nm and 50 $\mu$W at 1.135 $\mu$m. The Raman shift is 2913 $cm^{-1}$, in the spectral region of aliphatic CH vibrations. Acquisition time was 43 min, scan size 30 $\mu$m, scale bar 5 $\mu$m. Bright features are attributed to cellular constituents rich in aliphatic CH, such mitochondria.
Figure 8:
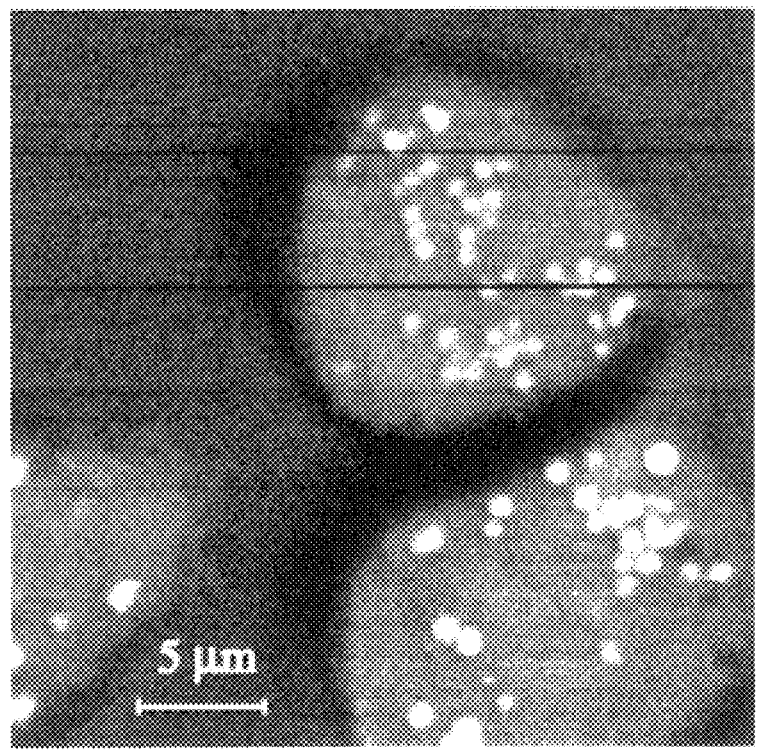
FIG. 8 is a CARS image of six live, unstained bacteria of the type Shewanella putrefaciens, strain CN-32, in deuterated water. Average powers incident at the sample were 100 $\mu$W at 855 nm and 100 $\mu$W at 1.134 $\mu$m. The Raman shift is 2878 $cm^{-1}$, in the spectral region of aliphatic CH vibrations. Acquisition time was 85 min, scan size 6 $\mu$m, scale bar 1 $\mu$m.

An experiment was conducted to demonstrate the present invention for imaging live cells. *Shewanella putrefaciens* strain CN-32 is a Gram negative bacterium. FIG. 7 and FIG. 8 show the CARS images of individual *Shewanella putrefacienas* cells when the laser frequencies were tuned to a Raman-shift to 2878 cm$^{-1}$, the frequency of aliphatic C—H stretching vibrations. Aliphatic C—H was expected to be abundant in the lipid bilayer of the cell membrane. The bacteria were grown on a glass cover slip, immersed in $D_2O$, and covered with another cover-slip. $D_2O$ was used to avoid sample heating as $H_2O$ has a weak overtone absorption with an onset at around 1.15 µm. The heating problem, if any, could easily be overcome by slightly shifting the wavelengths of both laser beams. For other systems, however, it was found that $H_2O$ can be used as a solvent without any heating effects being observable. When tuning the Raman-shift away from the aliphatic C—H stretching frequencies, all image contrast was lost. Detailed features within the small bacterial cells in FIG. 7 could not be resolved due to the insufficient lateral resolution, comparable to two-photon microscopy (cell width was smaller than 500 nm). However, the CARS image shows the high sensitivity enabling the imaging of unstained live bacterial cells.

The spatial resolving power for CARS on a biological specimen is also demonstrated in FIG. 8 for eucaryotic cells. FIG. 8 shows an image of live HeLa cells in an aqueous HEPES buffer solution, again with the Raman-shift tuned to the aliphatic C—H stretching region. Mitochondria, being rich in aliphatic C—H, appear as bright features of a size of approximately 1 µm within the cells. Tuning the Raman shift away from the frequency of aliphatic C—H stretching vibrations led to a complete loss of contrast. The average power levels used for recording the image shown in FIG. 8 were 50 µW at 853 nm and 50 µW at 1.135 µm. No photodamage of the living cells was observed during the image acquisition (43 min).

Directly Resonant Method and Apparatus

The SFG process requires an infrared beam at the molecular vibrational frequency, which is the same as the frequency difference which is used in CARS. Transmission of an IR beam through the sample is generally very limited since having the beam on resonance with a molecular vibration implies a very strong absorption. This is not a problem for identification of surface features, but of course prevents obtaining volume, or 3D, information.

EXAMPLE 3

An experiment was conduced to demonstrate the present invention using SFG.

An IR beam from the OPO/OPA at 3.5 micron wavelength was used, which is in resonance with hydrocarbon compounds. A near IR beam from a Ti:sapphire laser (about 850 nm) was used to produce a sum-frequency or signal beam in the red (about 670 nm). The energies of the IR beam can change significantly to achieve resonances with other molecules, although this might require changes to the OPO/OPA used to generate the light.

Figure 9:
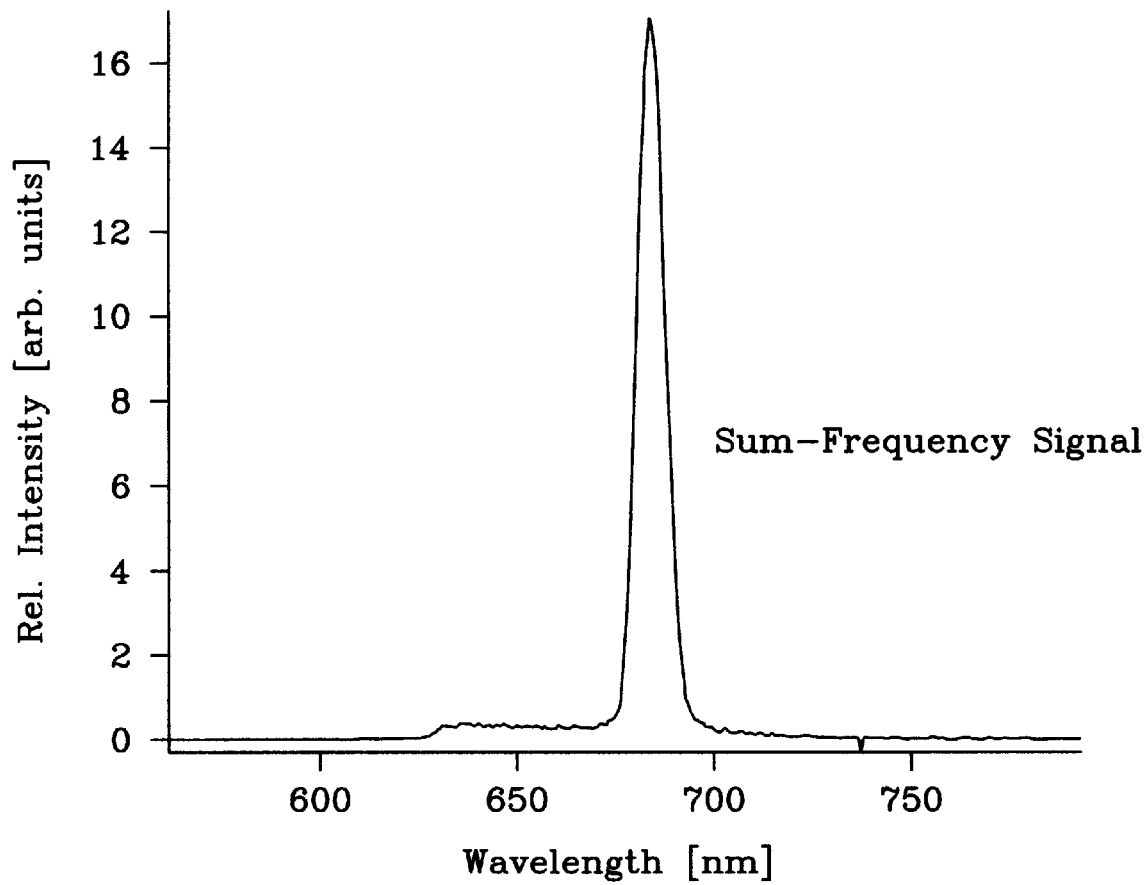
FIG. 9 is a SFG spectrum resulting from the excitation of a glass cover slip with two laser beams at 855 nm and 3.42 $\mu$m respectively.

The sum frequency beam was clearly seen using the microscope and its origin as a $\chi^{(2)}$ effect was verified by frequency measurement and by linear power dependence, as shown in FIG. 9.

EXAMPLE 4

Figure 10:
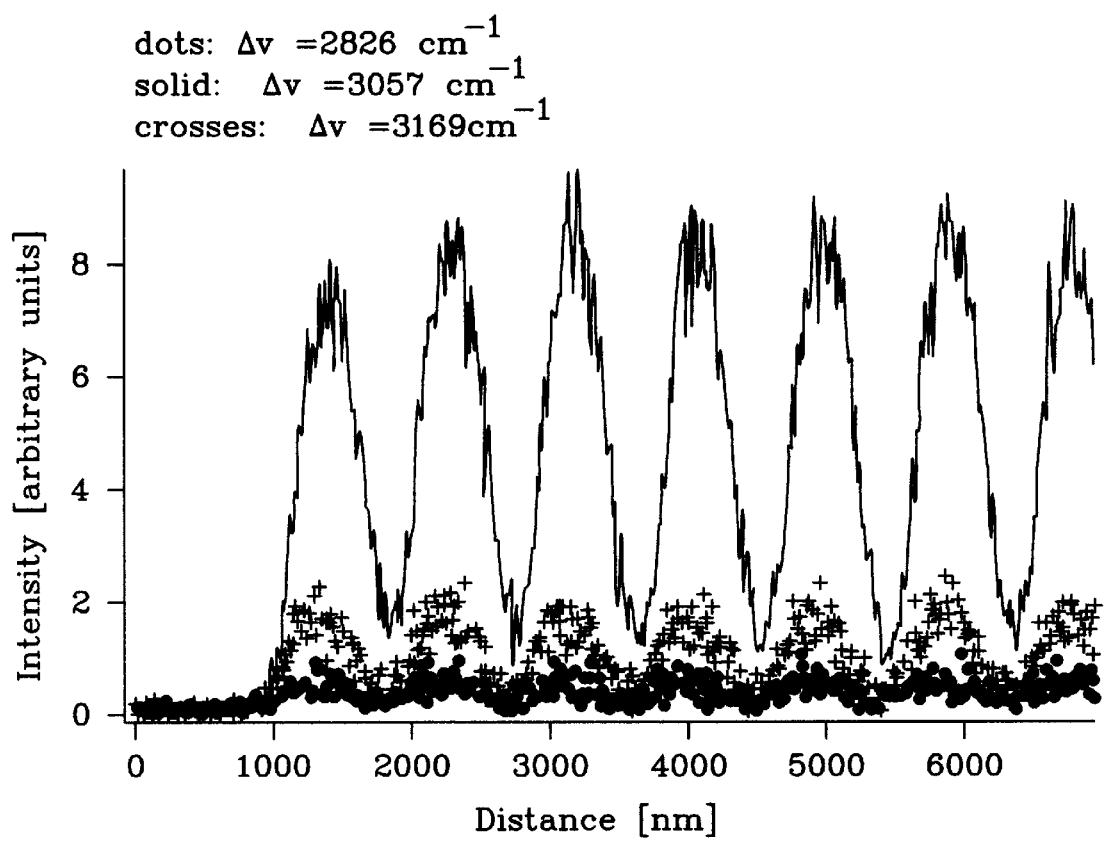
FIG. 10 shows intensity of a section of polystyrene bead image taken at several frequency separations.

An experiment was conducted to demonstrate spectral selectivity. By changing the wavelength difference between the two lasers, different species were selected. Sections of the polystyrene bead image taken at several frequency separations are shown in FIG. 10. The laser powers were adjusted to be the same for the data sets at different frequency shift. The most intense signal was with a frequency difference of the Stokes beam equal to the —CH resonance frequency of polystyrene at 3054 cm$^{-1}$. The intensity falls nearly to the background level between beads, demonstrating the spatial resolution observed in the image.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of creating a pixel, or spatially resolved image element, from at least two laser beams having first and second frequencies, the at least two laser beams spatially coincident on a sample producing a signal beam of a new frequency, the method comprising the steps of:
    a. directing the at least two laser beams in a substantially co-axial relationship through a lens providing a common focal spot on the sample;
    b. collecting the signal beam together with at least two residual beams from the at least two laser beams after passing through the sample;
    c. removing the at least two residual beams; and
    d. detecting the signal beam thereby creating said pixel.

2. The method as recited in claim 1, wherein said lens is an objective lens.

3. The method as recited in claim 2, further comprising the step of expanding the at least two laser beams for filling a back aperture of the objective lens.

4. The method as recited in claim 1, wherein said producing is with coherent anti-Stokes Raman scattering wherein a frequency difference between said at least two laser beams is in resonance with a vibrational frequency of the sample.

5. The method as recited in claim 4, wherein said at least two laser beams have wavelengths in the near infrared.

6. The method as recited in claim 1, wherein said producing is with sum frequency generation wherein a frequency of one of said at least two laser beams is in resonance with a molecular vibration of the sample.

7. The method as recited in claim 1, further comprising geometrically scanning said sample with respect to said common focal spot and obtaining a plurality of pixels and generating an image therefrom.

8. The method as recited in claim 1, further comprising scanning the common focal spot over the sample, by steering the at least two laser beams.

9. The method as recited in claim 1, further comprising changing the Raman vibrational frequency separation of at least two of the at least two pulsed laser beams for obtaining a vibrational property of the sample.

10. The method as recited in claim 1, wherein said vibrational frequency separation is less than 4000 cm$^{-1}$.

11. The method as recited in claim 1, further comprising the step of selecting a pulse width for the at least two laser beams, said pulse width infinite (continuous wave).

12. The method as recited in claim 1, further comprising the steps of
   a. selecting a finite pulse width and pulsing at least one of said at least two laser beams with said finite pulse width; and
   b. causing at least one of the at least two laser beams to temporally overlap the pulse of finite pulse width.

13. The method as recited in claim 12, wherein said pulse width is less than infinite, but longer than 10 femtoseconds.

14. The method as recited in claim 12, wherein said pulse width is shorter than 1 picosecond.

15. A system for creating a pixel from at least two laser beams having first and second frequencies, the at least two laser beams spatially coincident on a sample producing a signal beam of a third frequency, the system comprising:
   a. an optical director for directing the at least two laser beams in a substantially co-axial relationship through a microscope objective providing a focal spot on the sample
   b. a lens for collecting the signal beam together with at least two residual beams from the at least two laser beams after passing through the sample;
   c. a blocking filter for removing the at least two residual beams; and
   d. a detector for detecting the signal beam thereby creating said pixel.

16. The system as recited in claim 15, wherein said lens is an objective lens.

17. The system as recited in claim 16, further comprising a telescope for expanding the at least two laser beams for filling a back aperture of the objective lens.

18. The system as recited in claim 15, wherein said signal beam is obtained from a frequency difference or a sum frequency.

19. The system as recited in claim 15, further comprising a scanner for geometrically scanning said sample with respect to said at least two laser beams and obtaining a plurality of pixels and generating an image therefrom.

20. The system as recited in claim 15, further comprising scanning the common focal spot over the sample, by steering the at least two laser beams.

21. The system as recited in claim 15, further comprising a separator control for changing the difference in frequency between separation of at least two of the at least two pulsed laser beams for obtaining a vibrational property of the sample.

22. The system as recited in claim 15, wherein said difference in frequency is less than 4000 cm$^{-1}$.

23. The system as recited in claim 15, wherein a pulse width of said at least two laser beams is less them is less than infinite, but longer than 1 nanosecond.

24. The system as recited in claim 23, wherein said pulse width is from about 1 nanosecond to 1 picosecond.

25. The system as recited in claim 23, wherein said pulse width is shorter than 1 picosecond.

26. An apparatus for coherent anti-Stokes Raman scattering microscopic imaging, comprising:
   a. a pump wave laser that is a Ti:S mode-locked laser amplified with a regenerative amplifier for generating a pump wave;
   b. a second wave laser that is an optical parametric oscillator having a crystal of KNbO3 amplified with a portion of the pump wave;
   c. at least one telescope for adjusting the size and collimation of the laser beams, and a dichroic beam combiner for making them substantially coaxial;
   d. a microscope objective lens for focusing said pump wave laser and said second wave laser onto a sample; and
   e. a blocking filter that passes a detection signal to a detector.

27. A method of creating a pixel with Coherent Anti-Stokes Raman scattering having at least two substantially co-axial pulsed laser beams separated by a Raman vibrational frequency coincident on a sample, wherein the frequency difference between the at least two co-axial pulsed laser beams corresponds to a vibrational molecular resonance of the sample, the method comprising the steps of:
   a. directing the at least two co-axial pulsed laser beams through a microscope objective providing a focal spot on the sample;
   b. collecting a pulsed signal beam together with a residual beams from the at least two co-axial pulsed laser beams after passing through the sample;
   c. removing the residual beams; and
   d. detecting the pulsed signal beam thereby creating said pixel.

28. The method as recited in claim 27, further comprising geometrically scanning said sample with respect to said pulsed signal beam and obtaining a plurality of pixels and generating an image therefrom.

29. The method as recited in claim 27, further comprising geometrically scanning said sample with respect to said common focal spot and obtaining a plurality of pixels and generating an image therefrom.

30. The method as recited in claim 27, further comprising scanning the common focal spot over the sample, by steering the at least two laser beams.

31. The method as recited in claim 27, further comprising changing the Raman vibrational frequency separation of at least two of the at least two pulsed laser beams for obtaining a vibrational property of the sample.

32. A system for creating a pixel with Coherent Anti-Stokes Raman scattering having at least two parallel pulsed laser beams separated by a Raman vibrational frequency coincident on a sample, wherein the frequency difference between the at least two parallel pulsed laser beams corresponds to a vibrational molecular resonance of the sample, the system comprising:
   a. an optical director for directing the at least two parallel pulsed laser beams through a microscope objective providing a focal spot on the sample;
   b. a collection lens for collecting a pulsed signal beam together with a residual beam from the at least two parallel pulsed laser beams after passing through the sample;
   c. a blocking filter for removing the residual beam; and
   d. a detector for detecting the pulsed signal beam thereby creating said pixel.

33. The system as recited in claim 32, further comprising a scanner for geometrically scanning said sample with respect to said pulsed signal beam and obtaining a plurality of pixels and generating an image therefrom.

34. The system as recited in claim 32, further comprising geometrically scanning said sample with respect to said common focal spot and obtaining a plurality of pixels and generating an image therefrom.

35. The system as recited in claim 32, further comprising scanning the common focal spot over the sample, by steering the at least two laser beams.

36. The system as recited in claim 32, further comprising a separator control for changing the Raman vibrational frequency separation of at least two of the at least two pulsed laser beams for obtaining a vibrational property of the sample.

37. A method of creating a pixel, or spatially resolved image element, from at least two laser beams having first and second frequencies, the at least two laser beams spatially coincident on a sample producing a signal beam of a new frequency, the method having the steps of:
   a. directing the at least two laser beams through a lens providing a common focal spot on the sample;
   b. collecting the signal beam together with at least two residual beams from the at least two laser beams after passing through the sample;
   c. removing the at least two residual beams; and
   d. detecting the signal beam thereby creating said pixel; wherein the improvement comprises:
      at least one of said at least two laser beams has a wavelength in the range of from deep red (0.7 micron) to near infrared (2 micron).

38. The method as recited in claim 37, wherein said at least two laser beams have wavelengths in the range of from deep red to near infrared.

39. The method as recited in claim 37, wherein said at least two laser beams are coaxial.

40. The method as recited in claim 39 wherein said at least two laser beams fill a back aperture of said lens thereby providing said common focal spot of a size of less than 10 micron.

* * * * *